(12) United States Patent
Roemisch et al.

(10) Patent No.: US 7,892,842 B2
(45) Date of Patent: ***Feb. 22, 2011

(54) PROCEDURE FOR THE DETERMINATION OF THE ACTIVITY OF THE PROTEASE WHICH ACTIVATES FACTOR VII FROM PROTEIN SOLUTIONS

(75) Inventors: Juergen Roemisch, Gramatneusiedl (AT); Annette Feussner, Marburg (DE); Hans-Arnold Stoehr, Wetter (DE)

(73) Assignee: CSL Behring GmbH, Marburg (DE)

( * ) Notice: Subject to any disclaimer, the term of this patent is extended or adjusted under 35 U.S.C. 154(b) by 200 days.

This patent is subject to a terminal disclaimer.

(21) Appl. No.: 12/155,619

(22) Filed: Jun. 6, 2008

(65) Prior Publication Data

US 2009/0087864 A1 Apr. 2, 2009

Related U.S. Application Data

(60) Division of application No. 10/287,047, filed on Nov. 4, 2002, now abandoned, which is a continuation-in-part of application No. 09/591,338, filed on Jun. 9, 2000, now abandoned.

(30) Foreign Application Priority Data

Jun. 10, 1999 (DE) ................................. 199 26 531

(51) Int. Cl.
*G01N 33/86* (2006.01)
*G01N 33/53* (2006.01)

(52) U.S. Cl. ........................ 436/69; 435/7.1; 435/7.4; 435/7.6; 435/7.72; 435/7.91; 435/287.2; 435/966; 436/548; 436/164; 436/811

(58) Field of Classification Search ................... 435/2, 435/3, 6, 7.1, 7.4, 7.6, 7.72, 287.2, 966, 7.91; 436/518, 524, 528, 548, 164, 175, 811, 69; 536/23.2, 23.5

See application file for complete search history.

(56) References Cited

U.S. PATENT DOCUMENTS 4,784,950 A 11/1988 Hagen et al.

(Continued)

FOREIGN PATENT DOCUMENTS

CA 2269109 10/1999

(Continued)

OTHER PUBLICATIONS

Zhukov, Andrei et al., "Purification and Characterization of Hepsin From Rat Liver Microsomes," *Biochimica et Biophysica Acta*, vol. 1337, pp. 85-95 (1997).

(Continued)

*Primary Examiner*—Gailene R Gabel
(74) *Attorney, Agent, or Firm*—Finnegan, Henderson, Farabow, Garrett & Dunner, L.L.P.

(57) ABSTRACT

The present application relates to procedures for the determination of the activity of the protease which activates factor VII, also known as factor VII activating protease or FSAP. The application also relates to a method of detecting whether an individual has increased or lowered activity in the protease which activates factor VII compared to at least one standard sample, wherein the increased or lowered activity indicates an increased risk for disease or cardiovascular complications.

19 Claims, 2 Drawing Sheets

U.S. PATENT DOCUMENTS

| | | | |
|---|---|---|---|
| 5,175,087 | A | 12/1992 | Ranby et al. |
| 5,874,256 | A | 2/1999 | Bertina et al. |
| 5,968,759 | A | 10/1999 | Römisch et al. |
| 6,159,938 | A | 12/2000 | Gyorkos et al. |
| 6,242,173 | B1 | 6/2001 | Mann et al. |
| 6,528,299 | B1 | 3/2003 | Römisch et al. |
| 6,831,167 | B2 * | 12/2004 | Becker et al. ............... 536/23.2 |
| 2002/0110552 | A1 | 8/2002 | Römisch et al. |
| 2003/0077271 | A1 | 4/2003 | Römisch et al. |
| 2003/0124622 | A1 | 7/2003 | Römisch et al. |
| 2003/0215447 | A1 | 11/2003 | Römisch et al. |
| 2004/0063187 | A1 | 4/2004 | Römisch et al. |
| 2004/0186277 | A1 | 9/2004 | Römisch et al. |
| 2005/0032109 | A1 | 2/2005 | Römisch et al. |
| 2005/0202002 | A1 | 9/2005 | Römisch et al. |

FOREIGN PATENT DOCUMENTS

| | | |
|---|---|---|
| DE | 199 26 531.3 | 6/1999 |
| EP | 0 952 215 A2 | 10/1999 |
| EP | 0952 215 B1 | 4/2006 |
| FR | 2 504 921 | 11/1982 |
| WO | WO 82/63772 | 11/1982 |
| WO | WO 91/01497 | 2/1991 |

OTHER PUBLICATIONS

Choi-Miura, Nam-Ho et al., "Purification and Characterization of a Novel Hyaluronan-Binding Protein (PHBP) From Human Plasma: It Has Three EGF, a Kringle and a Serine Protease Domain, Similar to Hepatocyte Growth Factor Activator," *J. Biochem*, vol. 119, pp. 1157-1165 (1996).

Römisch, J. et al., "A Protease Isolated From Human Plasma Activating Factor VII Independent of Tissue Factor," *Blood Coagulation and Fibrinolysis*, vol. 10 (8), pp. 471-479 (1999).

Römisch, J. et al., "The FVII Activating Protease Cleaves Single-Chain Plasminogen Activators," *Haemostasis*, vol. 29, pp. 292-299 (1999).

Hunfeld, A. et al., "Detection of a Novel Plasma Serine Protease During Purification of Vitamin K-Dependent Coagulation Factors," *FEBS Letters*, vol. 456, pp. 290-294 (1999).

Hunfeld, A. et al., "Identification of the Thrombin-Like Activity of PCCs," (1998) (Abstract).

Römisch, J. et al., "A Protease Isolated From Plasma Which Activates FVII in a Tissue Factor Independent Manner But Inactivates FV and FVIII," (1999) (Abstract).

Etscheid, M. et al., "Characterization of a Novel Serine Protease From Plasma," (1999) (Abstract).

Römisch, J. et al., "The FVII Activating Protease Mediates Fibrinolytic Effects Activating Single-Chain Plasminogen Activators," (1999) (Abstract).

K. Laake et al., "Activation of Purified Plasma Factor VII by Human Plasmin, Plasma Kallikrein, And Activated Components of the Human Intrinsic Blood Coagulation System," *Thrombosis Research*, vol. 5(6); 759-772 (1974).

Y. Kazama et al., "Hepsin, a Putative Membrane-associated Serine Protease, Activates Human Factor VII and Initiates a Pathway of Blood Coagulation on the Cell Surface Leading to Thrombin Formation," *The Journal of Biological Chemistry*, vol. 270(1):66-72 (1995).

K. Kitamura, GenBank accession D49742 (1995).

K. Hashimoto et al., "Cloning of the cDNA for a Mouse Homologue of Human PHBP: A Novel Hyaluronan-Binding Protein," *Biol. Pharm. Bulletin*, vol. 20(11):1127-1300 (1997).

A. Hunfeld et al., 41$^{st}$ Annual Meeting of the GTH; Supplement II to vol. 74 A87 P113 (1997).

J.-I. Sumiya et al., "Isolation and Characterization of the Plasma Hyaluronan-Binding Protein (PHBP) Gene (*HABP2*)," *J. Biochem.*, vol. 122:983-990 (1997).

A. Hunfeld et al., 42$^{nd}$ Annual Meeting of the GTH; Supplement I to vol. 76 A101, P294 (1998).

M. Etscheid et al., 43$^{rd}$ Annual Meeting of the GTH; Supplement I to vol. 78 A42, P030 (1999).

J. Römisch et al., 43$^{rd}$ Annual Meeting of the GTH; Supplement I to vol. 78 A24, FV079 (1999).

J. Römisch et al., 43$^{rd}$ Annual Meeting of the GTH; Supplement I to vol. 78 A10, FV024 (1999).

A. Vostrov et al., "Plasma Hyaluronan-binding Protein Is a Serine Protease," *J. Biological Chemistry*, vol. 275(30):22978-22985 (2000).

J. Römisch et al., "Factor VII Activating Protease (FSAP): A Novel Protease in Hemostasis," *Biol. Chem.*, 383:1119-1124 (2002).

S.A. Choay et al., "Pharmaceutical Complex of Plasmin and Aprotinin-with Long Lasting Fibrinolytic Activity," Derwent Abstract, (2002).

* cited by examiner

PROCEDURE FOR THE DETERMINATION OF THE ACTIVITY OF THE PROTEASE WHICH ACTIVATES FACTOR VII FROM PROTEIN SOLUTIONS

This application is a divisional of U.S. patent application Ser. No. 10/287,047, filed Nov. 4, 2002, now abandoned; which is a continuation-in-part of U.S. patent application Ser. No. 09/591,338, filed Jun. 9, 2000, now abandoned. The application also claims priority to German Application No. 199 26 531.3, filed Jun. 10, 1999. Each of the above-identified applications is incorporated herein by reference, in its entirety.

The invention relates to a procedure for the qualitative and quantitative determination of the protease which activates factor VII in complex protein solutions such as plasma.

BACKGROUND OF THE CLAIMED INVENTION

The blood clotting system comprises two different cascade-like pathways for activating clotting factors which are present in the plasma. The intrinsic or the extrinsic pathway is used for initiating clotting, depending on the triggering mechanism.

When tissue is damaged, thromboplastin (tissue factor ("TF") with phospholipids) is exposed by the affected cells and initiates the extrinsic clotting pathway. The membrane located thromboplastin can bind both clotting factor VII (FVII) and circulating activated FVII (FVIIa). In the presence of calcium ions and lipids, this TF-FVIIa complex leads to the binding of FX, which is converted into its activated form (FXa) by limited proteolysis. FXa in turn leads, by activating prothrombin to form thrombin, to the formation of fibrin and ultimately to closure of the wound.

While further activation of the thromboplastin-bound FVII initially takes place autocatalytically, after the clotting cascade has been initiated, by FXa and thrombin, in particular, additional activation of the thromboplastin-bound FVII occurs, leading to marked reinforcement of the reaction cascade.

The administration of FVIIa or FVIIa-containing concentrates is used in certain clinical situations. The so-called FVIII-bypassing activity of FVIIa is used in patients who are suffering, for example, from hemophilia A and have developed antibodies against FVIII as a consequence of the administration of FVIII. According to presently available findings, FVIIa is well tolerated in this context and, while it does not lead to any tendency to thrombosis, it is suitable for ensuring that clotting takes place to a limited but adequate extent. Recombinant FVIIa is already being used therapeutically and prophylactically. FVII which has been isolated from blood plasma can also be activated and then used. Proteases such as thrombin can be used for this activation, however, these proteases strongly activate clotting and lead to the risk of a thrombosis. For this reason, subsequent removal or inactivation of thrombin is necessary and leads to yield losses. As a result of the risk of thrombosis which is associated with it, the use of FXa or FIIa (thrombin) is frequently contraindicated and only indicated in emergencies, e.g., in association with extreme loss of blood and unstoppable hemorrhages.

FVIIa is found in very low concentrations in the plasma of healthy subjects. Very little is known about the formation and origin of FVIIa which is circulating in the blood. Traces of thromboplastin which has been expressed or released in association with cell destruction might play a role in this context. Although it is known that factor XIIa, for example, can lead to FVII activation under certain conditions, the physiological relevance of this reaction has not yet been clarified.

Surprisingly, a FVII-activating protease, which differs from all the previously known proteases, has now been found in connection with fractionation of human plasma and certain prothrombin complex concentrates. Investigations into this protease have shown that it exhibits a particularly high amidolytic activity toward the peptide substrate S2288 (HD-isoleucyl-L-prolyl-L-arginine-pNA) from Chromogenix AB, Sweden. A particular feature of this protease is that the amidolytic activity is efficiently inhibited by aprotinin. Other inhibitors, such as the antithrombin III/heparin complex, are also suitable for the inhibition. On the other hand, its activity is increased by heparin and heparin-related substances such as heparin sulfate or dextran sulfate and calcium ions. Finally, it has been found that this protease is able, in a manner dependent on time and on its concentration, to convert FVII into FVIIa. This reaction, too, is inhibited by aprotinin.

The novel protease for activating the blood clotting factor VII is:

a) inhibited by the presence of aprotinin, b) increased in its activity by calcium ions and/or heparin or heparin-related substances, and c) in SDS-PAGE, on subsequent staining in the non-reduced state, has one or more bands in the molecular weight range from 50 to 75 kDa and in the reduced state has a band at 40 to 55 kDa and one or more bands in the molecular weight range from 10 to 35 kDa.

In the following text, the activated form of the protease is termed "protease" whereas the non-activated form is termed "proenzyme."

Further investigations with this protease have shown that, after enriching or isolation, it suffers from a rapid loss of activity, which was observed in a solution containing 20 mM tris, 0.15 M NaCl at a pH of 7.5. The addition of albumin at a concentration of 0.1% was not able to prevent the activity of the protease from decreasing by 50% after one hour at room temperature. On the other hand, very good stabilization of the protease was observed in a solution which was buffered to a pH of 6.5 with 50 mM Na citrate. If no particular stabilizers are added to the protease solution, slight to no losses in activity are observed if the solution is adjusted to a pH of between 4 and 7.2, preferably to a pH of between 5.0 and 7.0. However, it is expedient to add stabilizers to the solution, apart from citrate, such as glutamate, amino acids, such as arginine, glycine or lysine, calcium ions and sugars such as glucose, arabinose or mannose in quantities of 1-200 mmol/l, preferably in quantities of 5-100 mmol/l. Efficient stabilization was also achieved by adding glycols such as ethylene glycol or glycerol, with quantities of 5-80% by weight, preferably of 10-60% by weight, being used. The pH of the stabilized solution should then be between 4 and 9.

While the novel protease, and also the proenzyme, can be obtained by recombinant DNA methods or by production in, e.g., the milk of suitable transgenic animals, they can in particular be obtained by fractionation of blood plasma or of prothrombin complex (PPSB) concentrates. The starting material is first subjected to anion exchange chromatography, which is followed by an affinity chromatography of the elute. Heparin which is immobilized on a matrix, or a heparin-related substance such as heparan sulfate or dextran sulfate, is particularly suitable for the affinity chromatography. When such a chromatographic method is used, the novel protease and/or the proenzyme can be selectively bound and then eluted once again using known methods. The use of a spacer is advisable for coupling the ligand to the matrix. A heparin-lysine matrix has been found to be particularly suitable for isolating the novel protease.

In SDS-PAGE with subsequent staining, the protease which has been isolated by this method exhibits, in the non-reduced state, one to several bands which lie closely together in the molecular weight range of 55-75 kDa. Following reduction, one to several bands were observed in the molecular weight range of 15-35 kDa and one band was observed at 40-55 kDa. A further band between 60 and 65 kDa, which, after scanning and quantitative evaluation, constituted 5-10% was essentially achieved using an aprotinin matrix. As a result of the amidolytic cleavage of certain peptide substrates, the activity was described as being a thrombin-like activity. Hunfeld et al. did not find any influence on global clotting parameters such as prothrombin time, Quick or platelet aggregation.

The N-terminal sequencing of the protease described by Hunfeld et al. shows concordances with a protein whose cDNA was described by Choi-Miura et al. (*J. Biochem.* 119: 1157-1165 (1996)). In its primary structure, the corresponding protein exhibits homology with an enzyme termed hepatocyte growth factor activating enzyme (HGFA).

When the two bands of the present protease, which were isolated from SDS-PAGE under reducing conditions, were subjected to N-terminal sequencing, the following concordances were established:

| Molecular weight range of the band | Amino acid sequence | Author |
|---|---|---|
| 10-35 kDa | Ile-Tyr-Gly-Gly-Phe-Lys-Ser-Thr-Ala-Gly-Lys<br>(SEQ ID No. 1) | Protease of the present invention |
| 30 kDa | Ile-Tyr-Gly-Gly-Phe-Lys-Ser-Thr-Ala-Gly<br>(SEQ ID No. 2) | Hunfeld et al. |
| 17 kDa | Ile-Tyr-Gly-Gly-Phe-Lys-Ser-Thr-Ala-Gly-Lys-His<br>(SEQ ID No. 3) | Choi-Miura et al. |
| 40-55 kDa | Leu-Leu-Glu-Ser-Leu-Asp-Pro<br>(SEQ ID No. 4) | Protease of the present invention |
| 50 kDa | Ser-Leu-Asp-Pro<br>(SEQ ID No. 5) | Hunfeld et at. |
| 50 kDa | Ser-Leu-Leu-Glu-Ser-Leu-Asp-Pro-Trp-Thr-Pro-Asp<br>(SEQ ID No. 6) | Choi-Miura et al. | of the total protein, showed that non-activated proenzyme was also present. This result was supported by appropriate investigations using monoclonal antibodies against this protease. It was therefore concluded that the proenzyme of this protease can also be prepared, pasteurized and used by the method according to the invention. The proportion of the proenzyme to the weight of the total protein is indicated by the band between 60 and 65 kDa. Corresponding to the amino acid sequence which constitutes the activation region of the proenzyme, thrombin, kallikrein or FXIa are, in accordance with their substrate specificities, examples of suitable physiological activators of the proenzyme.

Some of the properties of the novel protease which have been described, namely the fact that it can be isolated from plasma or from Prothrombin complex (PPSB) concentrates which are derived from plasma, the inhibition of its amidolytic activity by aprotinin and the described migration behavior in SDS-PAGE, both in the reduced and in the non-reduced states, are reminiscent of a protease which was isolated by Hunfeld et al. (*Ann. Hematol.* 1997; 74; A87, 113; *Ann. Hematol.* 1998; 76; A101, P294 and Etscheid et al. *Ann. Hematol.* 1999, 78: A42) from a PPSB concentrate which was not defined in any more detail. In that case, the preparation Concordances are also found in other test results such as substrate specificity and the ability of the activity to be inhibited. Despite this, the above-mentioned proteins investigated by Hunfeld et al. and Choi-Miura et al. have not been reported to possess the property of activating FVII or activating other factors.

Because the novel protease can be used diagnostically and therapeutically, it is desirable to qualitatively and quantitatively detect the protease is complex protein solutions such as plasma.

DESCRIPTION OF THE CLAIMED INVENTION

German Patent Application 199 03 693, and its corresponding Canadian Patent Application 2,269,109, already discloses test systems and procedures for the qualitative and quantitative detection of the protease which activates blood clotting factor VII. These include chromogenic test procedures, which are based on the cleavage of labeled, low molecular weight peptide substrates and the photometric determination of the extinction occurring in this case, and test procedures in which the biological properties of the protease mentioned are utilized. In these procedures, the protease or its proenzyme can be detected in that it has a) an action which inactivates blood clotting factors VIII/VIIIa or V/Va; or b) an action which reduces the blood clotting times in global clotting tests; or c) an action which activates plasminogen activators; or d) an action which activates FVII.

In the test systems previously employed, however, the determination of the activity of the protease only leads to reliable results if the protease is present in a purified or enriched state and no interfering effects of impurities distort the measurement result. Very complex protein mixtures such as plasma or tissue fluids contain a large number of proteins which can prevent or at least hinder a specific qualitative and quantitative determination of the protease. Moreover, according to the present level of knowledge, the protease is present in the plasma especially as a proenzyme, such that activation to give the active protease is necessary for the purpose of the subsequent activity determination.

The investigation of the function and of the biological activity of the protease is of high interest. For example, a lowered antigen content and/or a disruption of the biological activity, for example due to a gene mutation, could indicate an increased risk of thrombosis. Therefore, the object of the present invention is to develop a procedure which makes possible the qualitative and quantitative determination, in a manner which is as simple and specific as possible, of one or more biological activities of the factor VII-activating protease.

It has now been found that these requirements are fulfilled by a procedure for the determination of the activity of the protease which activates the blood clotting factor VII in protein solutions, in which the protein solution comprising the protease and/or its proenzyme is incubated with a solid phase to which an antibody directed against the protease and/or its proenzyme has been coupled beforehand, and after washing the solid phase, the protease and/or its proenzyme fixed thereto, are incubated with reagents which allow for the determination of their activity.

Surprisingly, this determination procedure can be used not only on the protease in its activated form but also with its non-activated proenzyme. Although previous investigation results indicated that the protease circulates in plasma mainly as a proenzyme and, therefore, in order then to be able to display its biological activities, the proenzyme must be activated to the protease after being bound to the solid phase, it has now surprisingly been found that such an activation is not necessary. The proenzyme bound to the solid phase displays its biological activity in immobilized form in the same manner as the protease. A separate activation step is therefore unnecessary, allowing for more rapid and interference-free determination.

Activation of the proenzyme, however, can be done in order to ensure that the proenzyme bound to the solid phase has been completely activated.

Suitable solid phases are matrices known to the person skilled in the art, such as activated Sepharose® or Fraktogel®. Microtiter plates are preferably coated with antibodies directed against the protease or its proenzyme, which can be of polyclonal or monoclonal origin. Antibody fragments such as F(ab) or F(ab)$_2$ can also be used. Unlike the antigen test, in which a labeled second antibody is used for detection and quantification, the present invention can utilize chromogenic substrates which allow for the determination of the activity of the protease. A particularly preferred chromogenic substrate is S2288 from Chromogenix AB (H-D isoleucyl-L-prolyl-L-arginine-pNA×2 HCl), which, like similar compounds, shows significant concentration and time dependent increase in the absorption due to amidolysis of the substrate. Surprisingly, the protease retains its biological activities and properties even after binding to the antibody, namely the capability to activate FVII and plasminogen activators. The specific determination of the functionality of the protease from a complex protein solution is thereby possible.

In addition to the chromogenic substrates, the other substrates mentioned in Canadian Patent Application 2,269,109, such as S2765 (N-a-Cbo-D-Arg-Gly-Arg-pNA), also offer themselves for the activity determination, i.e., the inactivation of the blood clotting factors VIII/VIIIa or V/Va and also the activation of the FVII and the plasminogen activators. In this determination, for example, the proportion of activated factor VII can be determined by direct amidolysis of a chromogenic substrate which is specific for the FVII or by a coupled reaction such as the so-called FVIIa-rTF test. The activation of single-chain plasminogen activators (scuPA, single chain urokinase plasminogen activator or sctPA, single chain tissue plasminogen activator) can be simply monitored by substrate reaction of, for example, S2444 (pyroGlu-Gly-Arg-pNA×HCl). As described in Canadian Patent Application 2,269,109, substances can also be added for detection which stimulate the activity of the protease, for example, soluble calcium salts and/or heparin or substances related to heparin such as dextran sulfate.

Further investigations of the described process demonstrated its suitability for the detection or quantification of the FVII-activating protease in solutions, body fluids and cell or tissue extracts. Among these are the solutions containing this protease, such as intermediates of the preparation of the protease and cell culture supernatants, which are also obtained in the fermentation of appropriate cells for recombinant expression. Among these are also solutions, such as milk, which are obtained in the transgenic preparation of the protease or of the proenzyme.

The process is moreover suitable for the determination of the activity of the FVII activating protease in extracts of tissues or cells. Such a determination gives an indication about the presence of the protease activity or about potential pathological conditions in the case of over or underexpression of this protein.

A particular interest applies to the detection of the protease activities in body fluids, such as blood and plasma, seminal plasma, urine, cerebrospinal fluid, bronchioalveolar lavage, amniotic fluid, saliva or lacrimal fluid. A valuable supplement to present invention is the antigen determination system (e.g. ELISA) mentioned in Canadian Patent Application 2,269,109. With the aid of both determination systems, a more comprehensive picture can be obtained, for example, in the case of a disorder.

In the investigation of healthy blood donors, it was conspicuous that about 5-10% of the plasmas investigated had a markedly lower protease activity (approximately 30-50% of the 'average value'), compared with a standard (pool plasmas), as displayed in greater detail in FIG. 1. This information was supplemented by the fact that almost of all these donors had antigen contents in the normal range. This could indicate, for example, (heterozygotic) mutation(s) which would correspondingly influence the activity, but not the antigen content of a plasma sample. As a consequence, these donors could be a risk group for certain diseases and, if necessary, prophylactic measures could be taken early. This applies either to people who have increased or lowered activity levels. We found significantly increased activities of this protease (within in some cases a normal or slightly increased antigen content) in plasmas of patients with cardiac infarcts (see also FIG. 2) and stable and unstable angina pectoris compared with a group of healthy donors. As yet, it is still not clear whether an increase in the protease activity can be assessed as a cause of this condition or whether this more likely corresponds to a counterreaction of the body, in the sense of increased thrombolysis.

Figure 1A:
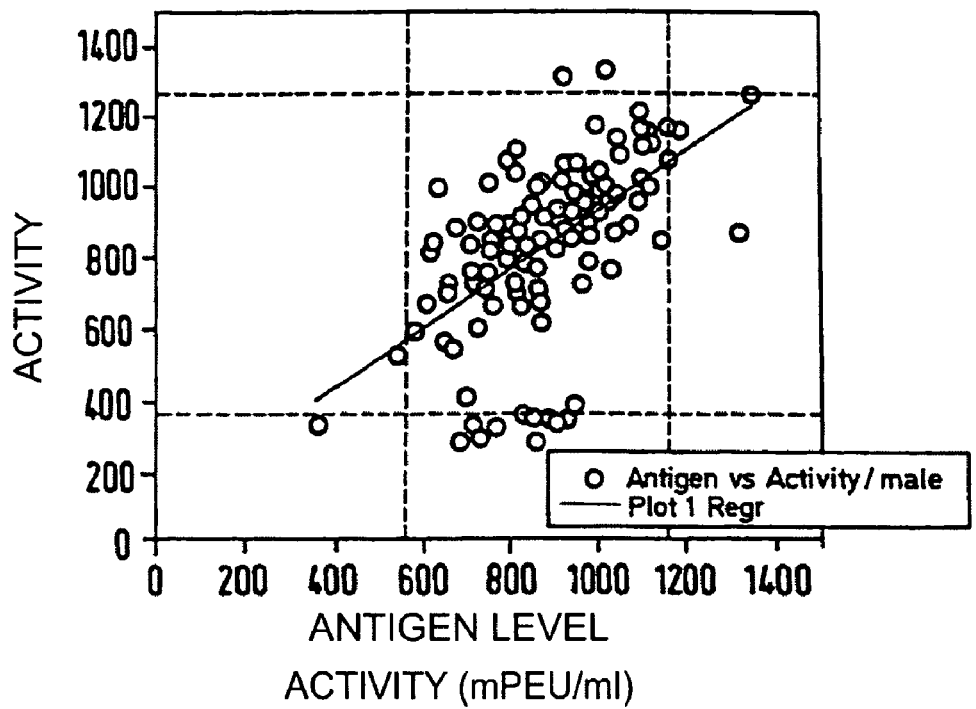
FIG. 1 shows protease activities (pPEU/ml) of healthy men (A) and women (B).
Figure 1B:
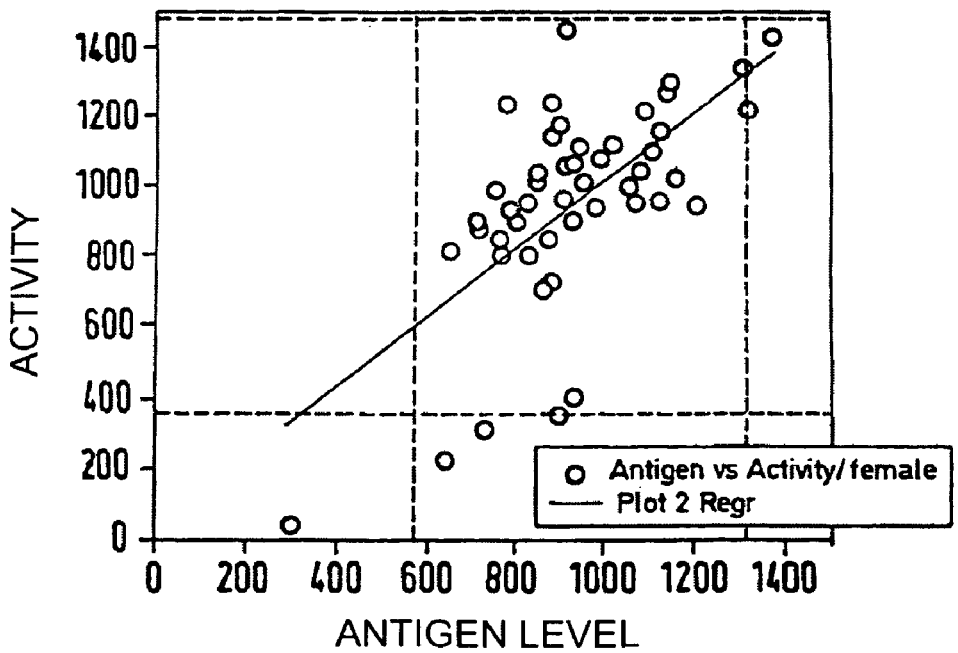
Figure 2A:
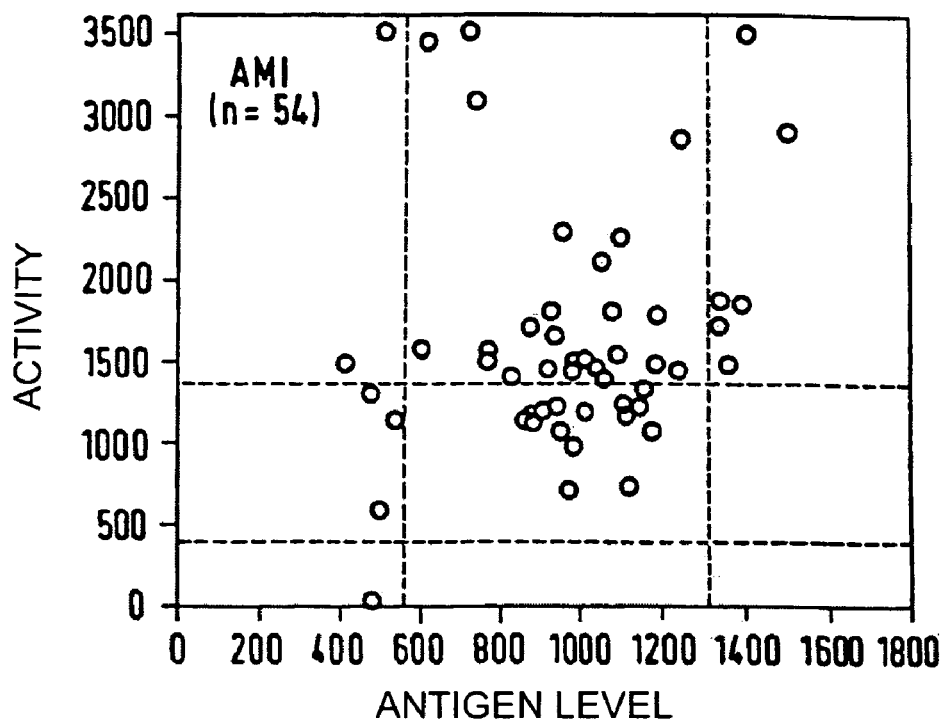
FIG. 2 shows protease activities (pPEU/ml) from patients with acute myocardial infarction (AMI) (A) and from healthy donors (B).
Figure 2B:
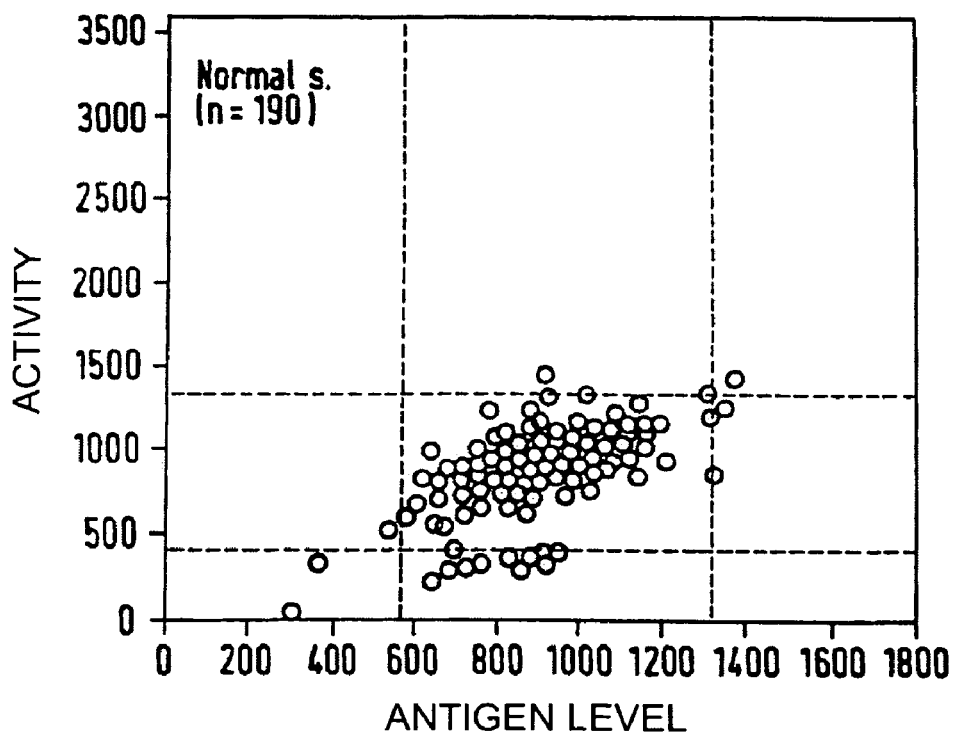

Apart from the physiological relevance of increased protease activities, this parameter can lead to early detection and can be used as a criterion of a change in the syndrome. This includes the diagnosis of further cardiovascular-associated complications.

Beyond these indications, the determination system described (also in combination with an antigen determination system) can also be used for diagnosis and therapeutic monitoring in the case of malignant diseases, inflammation, autoimmune diseases, vasculitis, respiratory defects or for the diagnosis of hemostasis (clotting and fibrinolysis), and also in the case of sepsis and associated reactions, such as disseminated intravasal clotting. Further application areas include the diagnosis of organ defects, such as cerebral, respiratory and kidney diseases. In patients with cirrhosis of the liver, we found significantly decreased activities of the protease, which in most cases were accompanied by decreased antigen levels.

Further investigations showed that in addition to a moderate increase in the antigen level in the plasma of healthy pregnant women, a marked increase in the protease activity is observed during the course of pregnancies, with the highest values in the third trimester. An absence of such an increase in the protease can be associated with a risk for the mother and child during the pregnancy, such as thromboembolic complications etc. up to and including premature birth and miscarriage or malformation of the fetus.

The invention is illustrated by the following examples:

EXAMPLE 1

Determination of Prourokinase

Microtiter plates (96 wells) were coated with a monoclonal antibody against the protease by pipetting 150 μl of a solution comprising 10 μg/ml of the monoclonal antibody into each hollow. After incubation at room temperature for 16 hours, the plates were washed several times. 100 μl of increasing concentrations of purified protease or various dilutions of a standard human plasma (SHPL) were in each case pipetted into the hollows. After incubation at 37° C., the solutions were removed by washing several times and the activities were determined.

50 μl of a prourokinase solution (10 μg/ml, American Diagnostica, US) were pipetted into each hollow, as were 50 μl of buffer, which contained 30 mM CaCl$_2$ and 100/ml of heparin. Two minutes later, a further 100 μl of buffer and 25 μl of the substrate S2444 (3 mM) were added. The increase in the absorption at 405 nm per minute was determined.

| Protease, purified (g/ml) | Δ mOD/min | SHPL (dilution) | Δ mOD/min |
|---|---|---|---|
| 0 | 0.4 | buffer | 0.4 |
| 0.1 | 7 | 1:200 | 0.4 |
| 0.2 | 12 | 1:100 | 0.9 |
| 0.4 | 18 | 1:50 | 7.5 |
| 0.6 | 22 | 1:33.3 | 8.4 |
| 0.8 | 24 | 1:25 | 15.2 |
| 1.0 | 27 | 1:20 | 24.8 |
| 2.0 | 34 | 1:10 | 31.2 |

EXAMPLE 2

Determination of the Activation of Factor VII

The coating of the microtiter plates and the incubation with the sample solutions was carried out as described in Example 1. Instead of the activation of the prourokinase, the activation of the factor VII was determined. To this end, in each case 50 μl of buffer, comprising 30 mM CaCl$_2$ and 100 IU/ml of heparin, were added to the hollows of the plate and incubated for 2 minutes at room temperature. After addition of a further 100 μl of buffer and 25 μl of Spectrozym® VIIa (3 mM, American Diagnostica/US), the) mOD/min was determined.

| Protease, purified (μg/ml) | ) mOD/min | SHPL (dilution) | ) mOD/min |
|---|---|---|---|
| 0 | 0.3 | buffer | 0.3 |
| 0.2 | 1.8 | 1:100 | 0.3 |
| 0.4 | 2.8 | 1:50 | 0.3 |
| 0.6 | 3.0 | 1:33.3 | 0.8 |
| 0.8 | 3.6 | 1:25 | 3.2 |
| 1.0 | 4.7 | 1:20 | 7.2 |
| 1.5 | 7.1 | 1:13.3 | 8.4 |
| 2.0 | 7.9 | 1:10 | 11.5 |

With the aid of these dilution series, it is possible to compare individual plasmas and to determine the functionality of the protease. By comparison with a standard human plasma which represents a pool of hundreds of individual plasmas, significant deviations from the norm can be detected. The activity thus found should ideally be set in the ratio to the antigen content which can be determined, for example, by means of ELISA.

If the amount of protease is known, then the specific activity of the protease and its proenzyme contained in the protein solution can be determined.

EXAMPLE 3

Determination of the Protease Activity in 190 Plasma Samples from Healthy Donors 190 citrated plasma samples from healthy people (140 men and 50 women), were investigated with the aid of the determination test described herein. In order to determine whether activities potentially differing from the average value of all investigated plasma samples accompanied a corresponding change in the protease antigen level, an ELISA was used as described in Canadian Patent Application 2,269,109. Such an ELISA for the detection of the protease as an antigen is feasible with the aid of monoclonal or polyclonal specific antibodies against this protease.

FIG. (1) shows the protease activities of the investigated healthy men (A) and women (B). It is clear that 5-10%, both men and women, show a markedly decreased activity compared with the average.

The protease activities (y-axis) and the antigen levels of the corresponding people (x-axis) are shown in the figure. The arbitrary "normal ranges" of the antigen and activity levels are in each case shown by horizontal and vertical lines as upper and lower limits of the parameters. The rectangles resulting therefrom (in each case in the center of the figure) accordingly represent the "normal ranges" of healthy donors. It is again particularly clear here that the majority of the samples having decreased activity were not accompanied by a corresponding reduction of the antigen levels. This could indicate a heterozygotic mutation (or several), i.e., for example about 50% of the protease molecules could be modified by one or more mutations such that a reaction with biological substrates is no longer guaranteed. In the case of a fibrinolytic importance of the protease, this could be associated with a risk of thrombosis (or of other diseases etc.) of this presently still "healthy" population, although in the minority of the samples investigated the values of the reduced protease activity, which go along very well with a reduced antigen content, are to be assessed as no less interesting, as obviously a dysregulation of the plasma availability of the protease is present, which can be associated with a comparable risk as described.

Accordingly, the detection of the protease activity, also in association with antigen determination, can be seen as a parameter for early recognition and prophylaxis/therapeutic control.

EXAMPLE 4

Determination of the Protease Activity in Plasma Samples from Pregnant Women

Citrated plasma samples from pregnant women were tested as described in Example 3. Samples were obtained at various times during pregnancy and then investigated.

The courses of two unproblematic pregnancies are shown in Table 1. A clear increase in the protease activity with duration of the pregnancy is detected, compared with the antigen contents of the protease show no increase to a moderate increase. An absence of this increased activity could be associated with problems for the mother and fetus.

Healthy (nonpregnant) women, on the other hand, show a continuous course of the protease activities (neither increased nor decreased, in the context of the test variations) during a corresponding observation period (not shown).

TABLE 1

| Trimester of pregnancy | Antigen (%) Pregnant women | | Activity (%) Pregnant women | |
|---|---|---|---|---|
| | 1 | 2 | 1 | 2 |
| I | 103 | 105 | 110 | 115 |
| II | 118 | 123 | 158 | 176 |
| III | 126 | 143 | 215 | 280 |

The percentage data relate to average values of healthy (nonpregnant) women (not shown).

EXAMPLE 5

Determination of the Protease Activity in Plasma Samples from Cardiac Infarct Patients Plasma samples from 54 patients with acute myocardial infarct were obtained on admission (before intensive treatment) to the emergency ward and used for routine analysis. Later, plasma residues (unthawed aliquots) were used for the quantification of the protease activities (and antigen contents).

FIG. (2) summarizes the results of the investigation. Compared with a group of healthy donors (B), significantly higher protease activities (and also the antigen contents) can be measured in the plasma of patients with acute myocardial infarct (A).

Accordingly, these parameters can be used for the early detection of an infarct, i.e., even in the case of stable and unstable angina pectoris. In patients with these coronary heart disorders, we also found significantly increased activities on average. The height of the measured values can make possible evaluation of the degree of severity of the disease or give valuable indications about the condition of the patient in the course of infarct and angina pectoris prophylaxis and therapy. Moreover, these parameters can be used for the assessment of other complications associated with the cardiovascular system.

---

We claim:

1. A method of detecting whether an individual has increased or lowered activity of the protease that activates blood clotting factor VII compared to at least one standard sample, comprising:
   (a) obtaining a body fluid sample from the individual,
   (b) determining the activity of the protease that activates blood clotting factor VII in the sample from the individual,
   (c) comparing the protease activity of the protease in the sample from the individual to the protease activity of the at least one standard sample, and
   (d) determining from (c) whether or not the individual has an increased or lowered activity of the protease that activates blood clotting factor VII compared to the at least one standard sample,
   wherein said increased activity indicates that the individual is suffering from a cardiac infarct or from stable or unstable angina, and wherein said lowered activity indicates that the individual has an increased risk of thrombosis.

2. The method of claim 1, wherein the protease activity is determined by measuring at least one of:
   inactivation of blood clotting factor VIII/VIIIa or V/Va;
   reduction of the time of blood clotting as measured in a global clotting test;
   activation of at least one plasminogen activator; or
   activation of FVII.

3. The method of claim 1, wherein the protease activity is determined by a method comprising:
   1) coupling an antibody that binds the protease to a solid phase;
   2) binding the protease to the antibody by incubating the sample with the solid phase;
   3) removing unbound protease by washing the solid phase;
   4) incubating the solid phase with a chromogenic substrate for the protease;
   5) detecting signal produced by the chromogenic substrate; and
   6) comparing the level of the detected signal with the level of signal from the standard.

4. The method of claim 3, wherein the activity is measured through photometric extinction of the signal produced by the chromogenic substrate.

5. The method of claim 3, wherein the antibody is a polyclonal antibody, a monoclonal antibody, or an F(ab) or F(ab)$_2$ antibody fragment.

6. The method of claim 3, wherein the chromogenic substrate is H-D-isoleucyl-L-prolyl-L-arginine-pNA×2 HCl or pyroGlu-Gly-Arg-pNA×HCl.

7. The method of claim 1, wherein the sample from the individual is a plasma sample.

8. The method of claim 7, wherein the at least one standard sample comprises a pool of plasmas.

9. The method of claim 1, wherein the protease activity is reduced by 50% or more compared to the at least one standard sample.

10. The method of claim 1, wherein the protease activity is increased compared to the at least one standard sample.

11. The method of claim 1, further comprising determining the antigen level of the protease that activates blood clotting factor VII in the sample and comparing the antigen level in the sample to the antigen level of the protease that activates blood clotting factor VII in at least one standard sample.

12. The method of claim 11, wherein the antigen level is determined by an enzyme-linked immunosorbent assay.

13. The method of claim 1, wherein the activity is determined by measuring activation of at least one plasminogen activator.

14. A method of detecting whether a pregnant individual has increased activity of the protease that activates blood clotting factor VII compared to at least one standard sample, comprising:
    (a) obtaining a body fluid sample from the individual,
    (b) determining the activity of the protease that activates blood clotting factor VII in the sample,
    (c) comparing the protease activity of the protease in the sample from the individual to the protease activity of the at least one standard sample, and
    (d) determining from (c) whether or not the individual has an increased activity of the protease that activates blood clotting factor VII compared to the at least one standard sample,
wherein an increased level of protease activity compared to the at least one standard sample indicates a reduced risk of thromboembolic complications.

15. The method of claim 14, further comprising determining the antigen level of the protease that activates blood clotting factor VII in the sample and comparing the antigen level in the sample to the antigen level of the protease that activates blood clotting factor VII in at least one standard sample.

16. The method of claim 14, wherein the activity is determined by measuring activation of at least one plasminogen activator.

17. A method of detecting whether an individual has 30-50% lower activity of the protease that activates blood clotting factor VII compared to at least one standard sample, comprising:
    (a) obtaining a body fluid sample from the individual,
    (b) determining the activity of the protease that activates blood clotting factor VII in the sample,
    (c) comparing the protease activity in the sample from the individual to the protease activity of the at least one standard sample, and
    (d) determining from (c) whether or not the individual has 30-50% lower activity of the protease that activates blood clotting factor VII compared to the at least one standard sample,
wherein said 30-50% lower activity indicates an increased risk for thrombosis.

18. The method of claim 17, further comprising determining the antigen level of the protease that activates blood clotting factor VII in the sample and comparing the antigen level in the sample to the antigen level of the protease that activates blood clotting factor VII in at least one standard sample.

19. The method of claim 17, wherein the activity is determined by measuring activation of at least one plasminogen activator.

* * * * *

SEQUENCE LISTING

```
<160> NUMBER OF SEQ ID NOS: 6

<210> SEQ ID NO 1
<211> LENGTH: 11
<212> TYPE: PRT
<213> ORGANISM: Homo sapiens

<400> SEQUENCE: 1

Ile Tyr Gly Gly Phe Lys Ser Thr Ala Gly Lys
1               5                   10

<210> SEQ ID NO 2
<211> LENGTH: 10
<212> TYPE: PRT
<213> ORGANISM: Homo sapiens
```

```
-continued

<400> SEQUENCE: 2

Ile Tyr Gly Gly Phe Lys Ser Thr Ala Gly
1               5                   10

<210> SEQ ID NO 3
<211> LENGTH: 12
<212> TYPE: PRT
<213> ORGANISM: Homo sapiens

<400> SEQUENCE: 3

Ile Tyr Gly Gly Phe Lys Ser Thr Ala Gly Lys His
1               5                   10

<210> SEQ ID NO 4
<211> LENGTH: 7
<212> TYPE: PRT
<213> ORGANISM: Homo sapiens

<400> SEQUENCE: 4

Leu Leu Glu Ser Leu Asp Pro
1               5

<210> SEQ ID NO 5
<211> LENGTH: 4
<212> TYPE: PRT
<213> ORGANISM: Homo sapiens

<400> SEQUENCE: 5

Ser Leu Asp Pro
1

<210> SEQ ID NO 6
<211> LENGTH: 12
<212> TYPE: PRT
<213> ORGANISM: Homo sapiens

<400> SEQUENCE: 6

Ser Leu Leu Glu Ser Leu Asp Pro Trp Thr Pro Asp
1               5                   10
```